United States Patent
Eshel et al.

(10) Patent No.: US 12,094,128 B2
(45) Date of Patent: Sep. 17, 2024

(54) ROBOT INTEGRATED SEGMENTAL TRACKING

(71) Applicant: Mazor Robotics Ltd., Caesarea (IL)

(72) Inventors: Itamar Eshel, Tzur Igal (IL); Ziv Seemann, Beit Ytzhack (IL); Adi Sandelson, Givatayim (IL); Gal Barazani, Haifa (IL); Nir Ofer, Tel Aviv-Jaffa (IL)

(73) Assignee: Mazor Robotics Ltd., Caesarea (IL)

( * ) Notice: Subject to any disclaimer, the term of this patent is extended or adjusted under 35 U.S.C. 154(b) by 373 days.

(21) Appl. No.: 17/591,769

(22) Filed: Feb. 3, 2022

(65) Prior Publication Data

US 2023/0245327 A1    Aug. 3, 2023

(51) Int. Cl.
*G06K 9/00* (2022.01)
*A61B 34/10* (2016.01)
(Continued)

(52) U.S. Cl.
CPC ............. *G06T 7/246* (2017.01); *A61B 34/10* (2016.02); *A61B 34/30* (2016.02); *G06T 11/00* (2013.01);
(Continued)

(58) Field of Classification Search
CPC ......... G06T 7/0012; G06T 2207/10028; G06T 2207/10016; G06T 7/73; G06T 7/75; G06T 7/246; G06T 7/33; G06T 2207/30196; G06T 7/277; G06T 2207/20081; G06T 7/248; G06T 7/251; G06T 7/70; G06T 2207/10132; G06T 2207/30244; G06T 7/11; G06T 7/149; G06T 7/74;
(Continued)

(56) References Cited

U.S. PATENT DOCUMENTS

2008/0050043 A1* 2/2008 Hermosillo Valadez ....................
G06T 7/0012
382/128
2008/0317329 A1* 12/2008 Shibuya ................ G06T 7/0004
382/149

(Continued)

OTHER PUBLICATIONS

International Search Report and Written Opinion for International (PCT) Patent Application No. PCT/IL2023/050073, dated Apr. 28, 2023, 15 pages.

*Primary Examiner* — Alex Kok S Liew
(74) *Attorney, Agent, or Firm* — Sheridan Ross P.C.

(57) ABSTRACT

Methods, systems, and devices for robot integrated segmental tracking are described. A system determines first positional information of one or more objects based on three-dimensional first image data captured by an imaging device, tracking information associated with the one or more objects, or both. The first positional information includes a real-time location of the one or more objects. The system generates an image including a graphical representation of the one or more objects. Generating the image includes positioning the graphical representation of the one or more objects based on a comparison result indicative of a deviation between the first positional information and reference positional information of the one or more objects. The reference positional information includes a registered location of the one or more objects. The system outputs an indication of the deviation between the first positional information and the reference positional information.

21 Claims, 4 Drawing Sheets

(51) Int. Cl.
*A61B 34/30* (2016.01)
*G06T 7/246* (2017.01)
*G06T 11/00* (2006.01)

(52) U.S. Cl.
CPC .................. *A61B 2034/105* (2016.02); *G06T 2207/10028* (2013.01); *G06T 2207/30204* (2013.01)

(58) Field of Classification Search
CPC ........... G06T 19/00; G06T 2207/10121; G06T 19/006; G06T 2207/10088; G06T 2207/30004; G06T 2207/30201; G06T 2207/10021; G06T 2207/20101; G06T 2207/30048; G06T 2210/41; G06T 1/00; G06T 17/00; G06T 2200/04; G06T 2207/10136; G06T 2207/20084; G06T 2207/20116; G06T 7/12; G06T 2200/24; G06T 11/60; G06T 7/40; G06T 7/254
See application file for complete search history.

(56) References Cited

U.S. PATENT DOCUMENTS

| | | | |
|---|---|---|---|
| 2010/0208963 A1* | 8/2010 | Kruecker | A61B 8/4254 |
| | | | 382/131 |
| 2012/0046521 A1 | 2/2012 | Hunter et al. | |
| 2014/0235998 A1 | 8/2014 | Kim et al. | |
| 2016/0022176 A1 | 1/2016 | Le Huec et al. | |
| 2019/0090955 A1 | 3/2019 | Singh et al. | |
| 2019/0357986 A1 | 11/2019 | Morgan et al. | |

* cited by examiner

ROBOT INTEGRATED SEGMENTAL TRACKING

FIELD OF TECHNOLOGY

The following relates to robotics assisted surgery, including techniques for tracking of the location of anatomical elements relative to a robotic system.

BACKGROUND

Surgical robots may assist a surgeon or other medical provider in carrying out a surgical procedure, or may complete one or more surgical procedures autonomously or semi-autonomously. Some surgical procedures may include monitoring the patient anatomy.

SUMMARY

The described techniques relate to improved methods, systems, devices, and apparatuses that support robot integrated segmental tracking. Generally, the described techniques provide for robotics assisted surgery that supports tracking the location of anatomical elements associated with the surgery.

A system includes: a processor; and a memory storing instructions thereon that, when executed by the processor, cause the processor to: determine first positional information of one or more objects based on three-dimensional first image data captured by an imaging device, tracking information associated with the one or more objects, or both, where the first positional information includes a real-time location of the one or more objects; generate an image including a graphical representation of the one or more objects, where generating the image includes positioning the graphical representation of the one or more objects based on a comparison result indicative of a deviation between the first positional information and reference positional information of the one or more objects, where the reference positional information includes a registered location of the one or more objects; and output an indication of the deviation between the first positional information and the reference positional information.

A method includes: determining first positional information of one or more objects based on three-dimensional first image data captured by an imaging device, tracking information associated with the one or more objects, or both, where the first positional information includes a real-time location of the one or more objects; generating an image including a graphical representation of the one or more objects, where generating the image includes positioning the graphical representation of the one or more objects based on a comparison result indicative of a deviation between the first positional information and reference positional information of the one or more objects, where the reference positional information includes a registered location of the one or more objects; and outputting an indication of the deviation between the first positional information and the reference positional information.

A system includes: an imaging device; a tracking device coupled to one or more objects; a processor; and a memory storing data thereon that, when processed by the processor, cause the processor to: determine first positional information of the one or more objects based on three-dimensional first image data captured by the imaging device, tracking information associated with the one or more objects, or both, where the first positional information includes a real-time location of the one or more objects; generate an image including a graphical representation of the one or more objects, where generating the image includes positioning the graphical representation of the one or more objects based on a comparison result indicative of a deviation between the first positional information and reference positional information of the one or more objects, where the reference positional information includes a registered location of the one or more objects; and output an indication of the deviation between the first positional information and the reference positional information.

In some examples of the systems and method described herein, the tracking information is associated with a tracking device coupled to the one or more objects; and the tracking information includes at least one of movement information, positional information, and orientation information associated with the tracking device.

In some examples of the systems and method described herein, the tracking device includes at least one of a spherical shaped element, a polygonal shaped element, a squircular shaped element, and a graphical marking.

In some examples of the systems and method described herein, the tracking device includes at least one substantially non-reflective surface.

In some examples of the systems and method described herein, the tracking information corresponds to a tracked area associated with the one or more objects; and the tracking information includes at least one of movement information, positional information, and orientation information associated with the tracked area.

In some examples of the systems and method described herein, the instructions are further executable by the processor to: track at least one of the movement information, the positional information, and the orientation information associated with the tracked area based on at least one of: a tracking device coupled to the one or more objects; and a graphical marking associated with the tracking device, the tracked area, or both. In some aspects, the graphical marking is included in the tracking device, included the tracked area, within a threshold distance of the tracked area, or any combination thereof.

In some examples of the systems and method described herein, the one or more objects includes a first object and a second object; and the tracking information is associated with at least one of: first tracking device coupled to the first object; a second tracking device coupled to the second object; a first tracked area associated with the first object; and a second tracked area associated with the second object.

In some examples of the systems and method described herein, the one or more objects include at least one anatomical element.

In some examples of the systems and method described herein, the deviation between the first positional information and the reference positional information includes at least one of: a distance value; an orientation value; and a movement value.

In some examples of the systems and method described herein, the first positional information and the reference positional information are associated with at least one of: a first coordinate system associated with a robot device included in the system; and a second coordinate system associated with the one or more objects.

In some examples of the systems and method described herein, the instructions are further executable by the processor to: maneuver a robotic arm of the system based on at least one of: a first value associated with the deviation; and a second value associated with compensating for the deviation.

In some examples of the systems and method described herein, the instructions are further executable by the processor to: control at least one surgical tool based on at least one of: a first value associated with the deviation; and a second value associated with compensating for the deviation.

In some examples of the systems and method described herein, the instructions are further executable by the processor to: update a surgical plan based on at least one of: a first value associated with the deviation; and a second value associated with compensating for the deviation.

DETAILED DESCRIPTION

Figure 1:
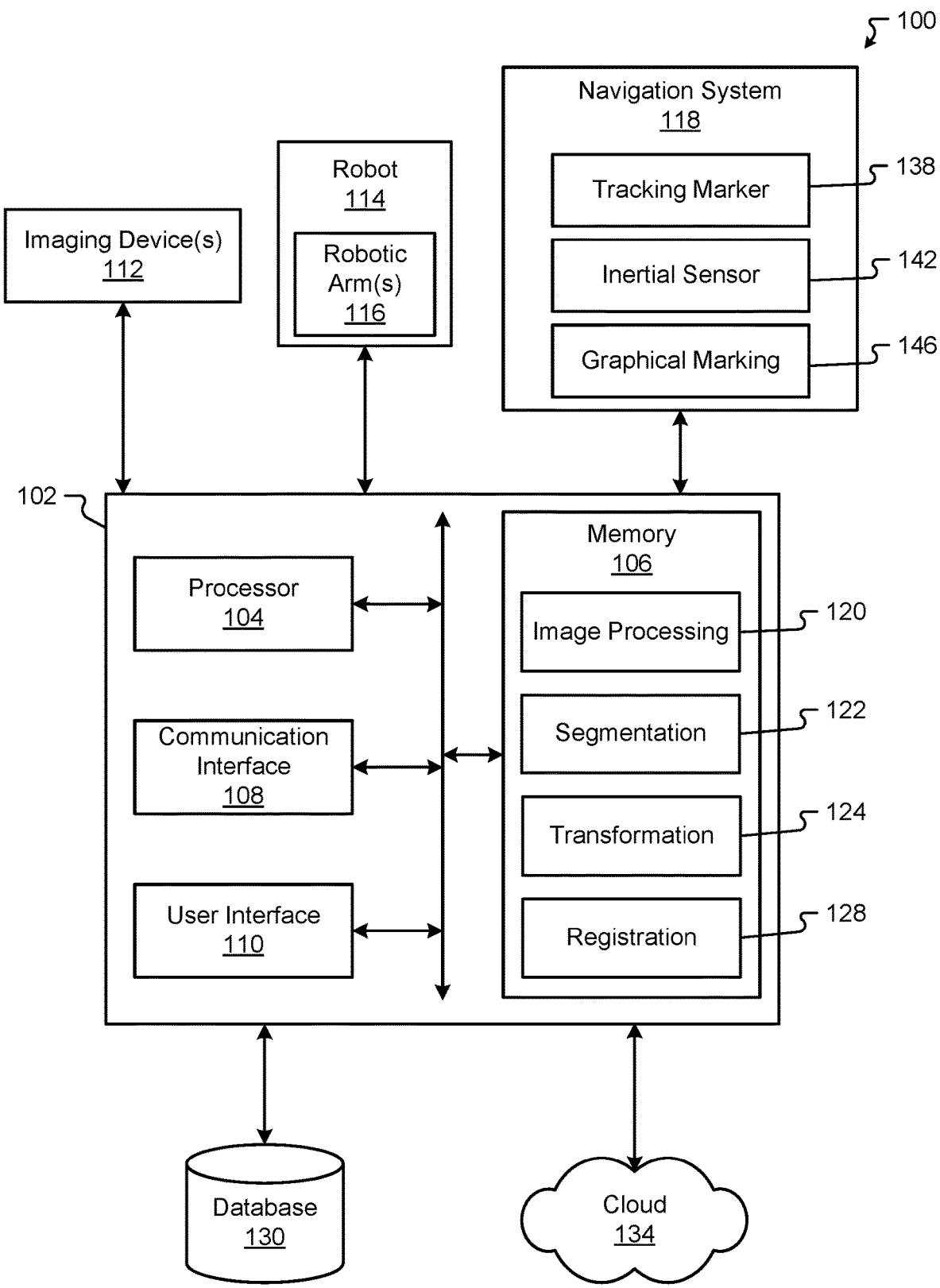
FIG. 1 illustrates an example of a system that supports robot integrated segmental tracking in accordance with aspects of the present disclosure.

It should be understood that various aspects disclosed herein may be combined in different combinations than the combinations specifically presented in the description and accompanying drawings. It should also be understood that, depending on the example or implementation, certain acts or events of any of the processes or methods described herein may be performed in a different sequence, and/or may be added, merged, or left out altogether (e.g., all described acts or events may not be necessary to carry out the disclosed techniques according to different implementations of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Alternatively or additionally, functions may be implemented using machine learning models, neural networks, artificial neural networks, or combinations thereof (alone or in combination with instructions). Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), graphics processing units (e.g., Nvidia GeForce RTX 2000-series processors, Nvidia GeForce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any implementations of the disclosure are explained in detail, it is to be understood that the disclosure is not limited in its application to the details of construction and the arrangement of components set forth in the following description or illustrated in the drawings. The disclosure is capable of other implementations and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

The terms proximal and distal are used in this disclosure with their conventional medical meanings, proximal being closer to the operator or user of the system, and further from the region of surgical interest in or on the patient, and distal being closer to the region of surgical interest in or on the patient, and further from the operator or user of the system.

In navigation-assisted or robotic-assisted surgeries, some systems (e.g., robotic systems) may register locations associated with the anatomy of a patient being operated upon, for example, relative to the system (e.g., register the locations with respect to a coordinate system associated with a surgical robot of the system, a coordinate system associated with the system, etc.). For example, some systems may incorporate an optical instrument or other marker placed on the anatomy of the patient (e.g., a vertebra of the spine), in which the optical instrument or marker is linked to or tracked by the navigation system.

Some systems may implement a single optical instrument fixed on an anatomical element (e.g., a vertebra of the spine) of the patient, leading to a possible decrease in accuracy of the registration. Further, in some cases, after registration of anatomical elements is complete, detecting whether a shift(s) has occurred between a coordinate system associated with the system and a coordinate system associated with the anatomical elements (e.g., associated with registered positions of the anatomical elements). For example, if an anatomical element has moved relative to coordinate system of the robotic system (e.g., shifted relative to the coordinate system) or moved relative to itself (e.g., shifted relative to a corresponding registered position), errors (e.g., implant location errors) may occur during a surgical operation.

Aspects of the present disclosure support utilizing an imaging device integrated with a system (e.g., a robotic system). Using the imaging device, the system may capture images for periodically assessing whether any shifts (e.g., between a coordinate system associated with the system and a coordinate system associated with the anatomical elements, between a registered position and/or orientation of an anatomical element and a real-time position and/or orientation of the anatomical element, etc.) have occurred. Accordingly, for example, the system may alert an operator of the system of any detected shifts. In some aspects, the system may provide notifications to the operator for maneuvering a robotic arm(s) in association with the surgical operation. The robotic arm(s), for example, may be coupled to the imaging device and/or a surgical tool.

The imaging device may be an image capture device (e.g., a camera). For example, the imaging device may be a camera device capable of capturing three-dimensional (3D) images (e.g., static and/or video images) of anatomical elements of the patient. In some aspects, the image capture device may be integrated with (e.g., electrically and/or mechanically coupled with) a robotic arm(s) of the system. In some other aspects, the image capture device may be integrated at other locations of the system. For example, the image capture device may be located at a stationary position of a room including the system, integrated with another device(s) (e.g., stationary or mobile) of the system, etc.

Using the imaging device, the system may compare real-time locations and previous locations of anatomical elements (e.g., organs, etc.) of the patient. In an example, the system may compare the real-time and previous locations of the anatomical elements using captured 3D images, for example, by scanning an entire 3D image(s) of the anatomy of the patient (e.g., in open surgery). For example, during open surgery, a relatively clear (e.g., unobstructed) line of sight to the anatomy and anatomy connectors is available, and the system may track both the anatomy and the anatomy connectors using the imaging device.

Additionally, or alternatively, the system may compare real-time and previous locations of the anatomical elements using 3D tracking information obtained from tracking devices (e.g., tracking markers) coupled to the anatomy (e.g., in minimally invasive surgery (MIS), open surgery, etc.). For example, aspects of the present disclosure support tracking multiple tracking devices coupled to the anatomy (e.g., multiple tracking devices attached to different respective anatomical elements). In some aspects, the tracking devices may be rigidly connected to the anatomy.

In some aspects, each tracking device (e.g., tracking marker) may include a spherical bead, a pin head, a graphical marking (e.g., a symbol, a black and white symbol, a pattern, etc.), etc. but is not limited thereto. For example, each tracking device may include any combination of a polygonal shaped element (e.g., square, triangular, pyramid, etc.), a squircular shaped element, a graphical marking, or the like.

The tracking devices (e.g., tracking markers) may be fully or partially non-reflective. For example, aspects of the present disclosure support a tracking marker having at least one surface that is substantially non-reflective. In some examples, the entirety (e.g., all surfaces of) the tracking marker may be substantially non-reflective. In some other alternative and/or additional aspects, the tracking devices (e.g., tracking markers) may be fully or partially reflective.

For example, aspects of the present disclosure support a tracking marker having at least one surface that is substantially reflective. In some examples, the entirety (e.g., all surfaces of) the tracking marker may be substantially reflective.

In some other alternative and/or additional aspects, the system may compare real-time and previous locations of the anatomical elements based on tracked areas of the anatomy. In some examples, the tracked areas may be indicated by graphical markings detectable by the imaging device. For example, each tracked area may be associated with a graphical marking included the tracked area. In some other aspects, the graphical marking may be within a threshold distance (e.g., configured using the system) of the tracked area.

Accordingly, for example, aspects of the present disclosure may support multiple layers of sensing (e.g., using captured 3D images, using multiple tracking elements, etc.). Using the multiple layers of sensing, the system may alert a user (e.g., an operator, a patient, etc.) of any shift between a registered anatomy location and an actual anatomy location. For example, the system may alert the user of any shift between registered locations of an anatomical element(s) (e.g., vertebra, vertebrae, etc.) and real-time locations of corresponding tracking element(s) (e.g., tracking markers, graphical markings, etc.).

Using the multiple layers of sensing, the system may compensate for such shifts. For example, the system may maneuver a robotic arm and/or a surgical tool so as to compensate for a deviation value associated with any such shifts. Accordingly, for example, the techniques described herein may support the prevention of surgical errors (e.g., incorrect placement of an implant, incorrect placement of a screw, etc.).

The techniques described herein may provide improved tracking compared to some tracking systems, for example, that rely on a navigation camera. For example, the system of the present disclosure may leverage 3D imaging capabilities (e.g., using a 3D camera device instead of a navigation camera), which may support achieving improved imaging resolution and accuracy. Further, aspects of the techniques described herein may support improved tracking and accuracy compared to some systems which rely on a single tracking marker as a reference, systems which rely on a single tracking marker for tracking only one anatomical element (e.g., a single vertebra), and systems which rely on reflective spheres susceptible to degraded tracking results due to contamination from bodily fluids (e.g., blood).

Aspects of the disclosure are initially described in the context of a robotic system. Examples of processes and signaling exchanges that support robot integrated segmental tracking are then described. Aspects of the disclosure are further illustrated by and described with reference to apparatus diagrams, system diagrams, and flowcharts that relate to robot integrated segmental tracking.

FIG. 1 illustrates an example of a system 100 that supports robot integrated segmental tracking in accordance with aspects of the present disclosure.

The system 100 may include a computing device 102, one or more imaging devices 112, a robot 114, a navigation system 118, a database 130, and/or a cloud network 134 (or other network such as, for example, a local network). Systems according to other implementations of the present disclosure may include more or fewer components than described with reference to the system 100. For example, the system 100 may omit or include additional instances of any of the imaging device 112, the robot 114, the navigation system 118, one or more components of the computing device 102, the database 130, and the cloud network 134.

The system 100 may support tracking optical trackers (e.g., tracking markers 138 described herein) positioned on or near one or more anatomical elements. The system 100 may support registering anatomical elements (and corresponding positional information, orientation information, dimension information, etc. thereof) to the navigation system 118. In some aspects, the system 100 may support controlling, maneuvering, and/or otherwise manipulating a surgical mount system, a surgical arm (e.g., a robotic arm 116 described herein), and/or surgical tools attached thereto based on the registration and/or the optical trackers.

The computing device 102 includes a processor 104, a memory 106, a communication interface 108, and a user interface 110. Computing devices according to other implementations of the present disclosure include more or fewer components than the computing device 102.

The processor 104 of the computing device 102 may be any processor described herein or any similar processor. The processor 104 may be configured to execute instructions stored in the memory 106, which instructions may cause the processor 104 to carry out one or more computing steps utilizing or based on data received from the imaging device 112, the robot 114, the navigation system 118, the database 130, and/or the cloud network 134.

The memory 106 may be or may include RAM, DRAM, SDRAM, other solid-state memory, any memory described herein, or any other tangible, non-transitory memory for storing computer-readable data and/or instructions. The memory 106 may store information or data useful for completing, for example, any step of the method 400 described herein, or of any other methods. The memory 106 may store, for example, instructions and/or machine learning models that support one or more functions of the robot 114. For instance, the memory 106 may store content (e.g., instructions and/or machine learning models) that, when executed by the processor 104, enable image processing 120, segmentation 122, transformation 124, and/or registration 128. Such content, if provided as in instruction, may, in some implementations, be organized into one or more applications, modules, packages, layers, or engines. Alternatively or additionally, the memory 106 may store other types of content or data (e.g., machine learning models, artificial neural networks, deep neural networks, etc.) that can be processed by the processor 104 to carry out the various method and features described herein. Thus, although various contents of memory 106 may be described as instructions, it should be appreciated that functionality described herein can be achieved through use of instructions, algorithms, and/or machine learning models. The data, algorithms, and/or instructions may cause the processor 104 to manipulate data stored in the memory 106 and/or received from or via the imaging device 112, the robot 114, the database 130, and/or the cloud network 134.

The computing device 102 may also include a communication interface 108. The communication interface 108 may be used for receiving image data or other information from an external source (such as the imaging device 112, the robot 114, the navigation system 118, the database 130, the cloud network 134, and/or any other system or component not part of the system 100), and/or for transmitting instructions, images, or other information to an external system or device (e.g., another computing device 102, the imaging device 112, the robot 114, the navigation system 118, the database 130, the cloud network 134, and/or any other system or component not part of the system 100). The communication interface 108 may include one or more wired interfaces (e.g., a USB port, an Ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some implementations, the communication interface 108 may support communications between the device 102 and one or more other processors 104 or computing devices 102, whether to reduce the time needed to accomplish a computing-intensive task or for any other reason.

The computing device 102 may also include one or more user interfaces 110. The user interface 110 may be or may include a keyboard, mouse, trackball, monitor, television, screen, touchscreen, a microphone, a speaker, and/or any other device for receiving information from a user and/or for providing information to a user. The user interface 110 may be used, for example, to receive a user selection or other user input regarding any step of any method described herein. In some aspects, the user interface 110 may support providing audio, visual, and/or haptic notifications.

Notwithstanding the foregoing, any input (e.g., required, optional, etc.) for any step of any method described herein may be generated automatically by the system 100 (e.g., by the processor 104 or another component of the system 100) or received by the system 100 from a source external to the system 100. In some implementations, the user interface 110 support inputs from a surgeon or other user (e.g., an operator, a technician, etc.) to modify instructions to be executed by the processor 104 according to one or more implementations of the present disclosure, and/or to modify or adjust a setting of other information displayed on the user interface 110 or corresponding thereto.

Although the user interface 110 is shown as part of the computing device 102, in some implementations, the user interface 110 may be housed separately from one or more remaining components of the computing device 102. In some implementations, the user interface 110 may be located proximate one or more other components of the computing device 102, while in other implementations, the user interface 110 may be located remotely from one or more other components of the computer device 102. Accordingly, for example, in such example implementations, the user interface 110 may communicate with the computing device 102 using wired and/or wireless communications.

The imaging device 112 may be operable to image anatomical feature(s) (e.g., a bone, veins, tissue, etc.) and/or other aspects of patient anatomy to yield image data (e.g., image data depicting or corresponding to a bone, veins, tissue, etc.). "Image data" as used herein refers to the data generated or captured by an imaging device 112, including in a machine-readable form, a graphical/visual form, and in any other form. In various examples, the image data include data corresponding to an anatomical feature of a patient, or to a portion thereof. The image data may be or may include a preoperative image, an intraoperative image, a postoperative image, or an image taken independently of any surgical procedure.

The imaging device 112 may be capable of capturing a 2D image(s) and/or 3D image(s) to yield the image data. In some aspects, the imaging device 112 may support motion tracking. For example, the imaging device 112 may be a 3D camera (e.g., a 3D depth camera; a camera capable of capturing 3D images, 3D motion, w3D camera capable of providing a full 3D image of an entire anatomy in a multi-dimensional space, etc.) or a stereo camera, and the imaging device 112 may support 3D motion tracking using 3D image coordinates and a marker (e.g., a tracking marker 138 described herein). In another example, the imaging device 112 may be a 2D camera (e.g., capable of capturing 2D images, 2D motion, etc.), but support 3D motion tracking using 2D image coordinates and a marker (e.g., a tracking marker 138 described herein).

The imaging device 112 may be or include, for example, an ultrasound scanner (which may include, for example, a physically separate transducer and receiver, or a single ultrasound transceiver), an O-arm, a C-arm, a G-arm, or any other device utilizing X-ray-based imaging (e.g., a fluoroscope, a CT scanner, or other X-ray machine), a magnetic resonance imaging (MRI) scanner, an optical coherence tomography (OCT) scanner, an endoscope, a microscope, an optical camera, a thermographic camera (e.g., an infrared camera), a radar system (which may include, for example, a transmitter, a receiver, a processor, and one or more antennae), or any other imaging device 112 suitable for obtaining images of an anatomical feature of a patient. The imaging device 112 may be contained entirely within a single housing, or include a transmitter/emitter and a receiver/detector that are in separate housings or are otherwise physically separated.

In some implementations, the imaging device 112 may include more than one imaging device 112. For example, an imaging device 112 may provide first image data (e.g., a first image or set of images) at a first temporal instance, a first temporal period, etc., and another imaging device 112 may provide second image data (e.g., a second image or set of images) at the same temporal instance, the same temporal period, at a different temporal instance, at a different temporal period, etc. In still other implementations, the same imaging device 112 may be used to provide both the first image data and the second image data, and/or any other image data described herein. In some implementations, an imaging device 112 may be used to obtain first image data (e.g., a first image) at a first time, and another imaging device 112 may be used to obtain second image data (e.g., a second image) at a second time after the first time.

The imaging device 112 may be operable to generate a stream of image data. For example, the imaging device 112 may be configured to operate with an open shutter, or with a shutter that continuously alternates between open and shut so as to capture successive images. For purposes of the present disclosure, unless specified otherwise, image data may be considered to be continuous and/or provided as an image data stream if the image data represents two or more frames per second.

The robot 114 may be any surgical robot or surgical robotic system. The robot 114 may be or include, for example, the Mazor X™ Stealth Edition robotic guidance system. The robot 114 may be configured to position the imaging device 112 at one or more precise position(s) and orientation(s), and/or to return the imaging device 112 to the same position(s) and orientation(s) at a later point in time. The robot 114 may additionally or alternatively be configured to manipulate a surgical tool (with or without guidance from the navigation system 118) in association with accomplishing or assisting with a surgical task. In some implementations, the robot 114 may be configured to hold and/or manipulate an anatomical element during or in connection with a surgical procedure.

The robot 114 may include one or more robotic arms 116. In some implementations, the robot 114 may include two or more robotic arms 116. In some implementations, one or more robotic arms 116 may be used to hold and/or maneuver the imaging device 112. In some implementations, one or more robotic arms 116 may be used to hold and/or maneuver a surgical tool. In some aspects, a robotic arm 116 may hold the imaging device 112 and/or be coupled to (e.g., electrically and/or mechanically) to the imaging device 112, and another robotic arm 116 may hold the surgical tool and/or be coupled to the surgical tool.

In implementations where the imaging device 112 includes two or more physically separate components (e.g., a transmitter and receiver), one robotic arm 116 may hold one such component, and another robotic arm 116 may hold another such component. In the example of multiple robotic arms 116, each robotic arm 116 may be positioned and/or controlled independent one another. The robotic arms 116 may be controlled in a single, shared coordinate space, or in separate coordinate spaces.

The robot 114, together with the robotic arm 116, may have multiple degrees of freedom (e.g., one, two, three, four, five, six, seven, or more degrees of freedom). Further, the robotic arm 116 may be positioned or positionable in any pose, plane, and/or focal point. The term "pose" may refer to a position and an orientation relative to a coordinate system. As a result, an imaging device 112, surgical tool, or other object held by the robot 114 (or, more specifically, by the robotic arm 116) may be precisely positionable in one or more positions and/or orientations.

The robotic arm(s) 116 include one or more sensors that enable the processor 104 (or a processor of the robot 114) to determine a precise pose in space of the robotic arm(s) 116 (as well as any object or element held by or secured to the robotic arm).

In some implementations, reference markers (e.g., navigation markers) may be placed on the robot 114 (including, e.g., on the robotic arm 116), the imaging device 112, or any other object in the surgical space. The reference markers may be tracked by the navigation system 118, and the results of the tracking may be used by the robot 114 and/or by an operator of the system 100 or any component thereof. In some implementations, the navigation system 118 can be used to track other components of the system (e.g., imaging device 112, robotic arm 116, surgical tools), and the system can operate without the use of the robot 114 (e.g., with the surgeon manually manipulating the imaging device 112 and/or one or more surgical tools, based on information and/or instructions generated by the navigation system 118, for example).

The navigation system 118 may provide navigation for a surgeon and/or a surgical robot during an operation. The navigation system 118 may be any now-known or future-developed navigation system, including, for example, the Medtronic StealthStation™ S8 surgical navigation system or any successor thereof. The navigation system 118 may include one or more imaging devices 112 (e.g., cameras) or other sensor(s) for tracking one or more reference markers, tracking markers 138 (also referred to herein as navigated trackers), graphical markings 146, target areas, or other objects within the operating room or other room in which some or all of the system 100 is located. imaging devices 112 may be optical cameras, infrared cameras, or other cameras. In some implementations, the navigation system 118 include one or more electromagnetic sensors.

In various implementations, the navigation system 118 may be used to track a position and orientation (e.g., a pose) of the imaging device 112, the robot 114 and/or robotic arm 116, and/or one or more surgical tools (or, more particularly, to track a pose of a tracking marker 138 attached, directly or indirectly, in fixed relation to the one or more of the foregoing). In some implementations, the navigation system 118 may use the imaging device 112 and/or data captured using the imaging device 112 to track the reference markers, tracking markers 138, graphical markings 146, target areas, or other objects within the operating room. The navigation system 118 may include a display for displaying one or more images from an external source (e.g., the computing device 102, imaging device 112, or other source) or for displaying an image and/or video stream from the one or more imaging devices 112 (e.g., cameras) or other sensors of the navigation system 118.

In some implementations, the system 100 can operate without the use of the navigation system 118. The navigation system 118 may be configured to provide guidance to a surgeon or other user (e.g., an operator, a technician, etc.) of the system 100 or a component thereof, to the robot 114, or to any other element of the system 100 regarding, for example, a pose of one or more anatomical elements, whether or not a tool is in the proper trajectory (e.g., a trajectory associated with a surgical procedure), and/or how to move a tool into the proper trajectory to carry out a surgical task according to a preoperative or other surgical plan.

The navigation system 118 may include one or more tracking markers 138. The tracking markers 138 may assist the navigation system 118 in determining one or more poses (e.g., positions and/or orientations) of one or more anatomical elements (e.g., vertebrae, ribs, soft tissues). The tracking markers 138 may be disposed on or proximate to one or more anatomical elements. In some implementations, the tracking markers 138 may be positioned in other areas in the surgical environment. For example, the tracking markers 138 may be positioned on other portions of the patient a known physical distance from the one or more anatomical elements, on or proximate one or more imaging devices 112, on or proximate one or more robotic arms 116, combinations thereof, and/or the like. The number and/or density of the number of tracking markers 138 disposed on, proximate to, or otherwise used to identify the one or more anatomical elements may be changed, altered, or otherwise chosen depending upon, for example, the type of anatomical element, the type of surgery or surgical procedure, combinations thereof, and/or the like.

The tracking markers 138 may be or may include optical components (e.g., elements that provide visual indicia) that may assist the navigation system 118 in determining a location of each of the tracking markers 138 within the surgical environment (e.g., relative to other tracking markers, relative to one or more anatomical elements, relative to other components of the system 100, combinations thereof, and/or the like). For example, the tracking markers 138 may include graphical markings 146. The graphical markings 146 may include any combination of symbols, patterns, identifiable information, etc. For example, a graphical marking 146 may be a black and white symbol, a pattern, etc.

In some aspects, the graphical markings 146 may be formed of a non-reflective material. In some other aspects, the graphical markings 146 may be formed of a reflective material. In some aspects, a graphical marking 146 may be printed or etched onto a tracking marker 138. The graphical markings 146 may be detectable by the navigation system 118 (e.g., using the imaging device 112).

In some aspects, the tracking markers 138 may be substantially non-reflective. In some examples, the tracking markers 138 may each include at least one substantially non-reflective surface. In another example, the entirety (e.g., all surfaces of) each tracking marker 138 may be substantially non-reflective.

In some other aspects, the tracking markers 138 may be reflective. For example, the tracking markers 138 may each be reflective, luminescent, or otherwise provide a visual indicator capable of being captured by the navigation system 118 (e.g., using the imaging device 112) to determine the pose of the tracking markers 138. In some implementations, the tracking markers 138 may include light emitting diodes (LEDs) and/or infrared light emitting diodes (IREDs) that emit visible light or other forms of electromagnetic radiation at various frequencies.

In some aspects, the tracking markers 138 may be a spherical bead, a pin head, etc. In an example, each tracking device 138 may include any combination of a polygonal shaped element (e.g., square, triangular, pyramid, etc.), a squircular shaped element, a graphical marking 146, or the like.

In at least one implementation, the tracking markers 138 include optical spheres (e.g., spheres with a 1 millimeter (mm), 2 mm, 3 mm, 4 mm, 5 mm, 6 mm, 7 mm, 8 mm, 9 mm, or 10 mm radius, or spheres with smaller or larger radii). The optical sphere size may be based on, for example, the type of anatomical element on which or proximate to which the sphere is placed, the type of surgery or surgical procedure, combinations thereof, and/or the like.

In some implementations, the tracking markers 138 may passively and/or actively generate indicia to assist the navigation system 118 in identifying the tracking markers 138. For instance, the tracking markers 138 with LEDs and/or IREDs may be wired or wirelessly connected to a controller, processor, or other computing device (e.g., a computing device 102) that generate and send signals that selectively illuminate the tracking markers 138. The signals may cause the tracking markers 138 to provide indicia at various frequencies, patterns, pulse rates/duty cycles, and/or intensities (e.g., color intensity, brightness intensity). In some implementations, the tracking markers 138 may be illuminated based on a surgical plan, the type of surgery or surgical procedure, the requirements of the navigation system 118 (e.g., the illumination occurs when the navigation system 118 or a user like a surgeon determines that the pose of one or more tracking markers 138 has not been determined), combinations thereof, and/or the like.

The navigation system 118 may include one or more inertial sensors 142 capable of measuring and/or recording movement information associated with an object (e.g., an anatomical element). The inertial sensors 142 may measure forces to, changes in angular momentum of, and/or changes in orientation (e.g., changes in pitch, yaw, and/or roll) of itself or of a component (e.g., an anatomical element) to which the inertial sensor 142 is attached. For instance, the inertial sensor 142 may measure the rotation or other movement of an object (e.g., an anatomical element) to which the inertial sensor 142 is attached when the object moves (e.g., when the object rotates, when the object experiences a force, etc.). In some implementations, the inertial sensor 142 may be or may include an inertial measurement unit (IMU). The IMU may be or may include accelerometers, gyroscopes, magnetometers, combinations thereof, and/or other components for detecting the movement of the inertial sensor 142.

The inertial sensors 142 may be positioned on (e.g., coupled to) one or more anatomical elements (e.g., vertebrae, ribs, other bones, etc.) or positioned a known physical distance therefrom. As such, the computing device 102 may convert or transform the movement of the inertial sensors 142 into an associated movement of an anatomical element to which the inertial sensors 142 is attached or of an anatomical element proximate the inertial sensors 142. The conversion or transformation may be based on the physical relationship between the inertial sensors 142 and the anatomical element (e.g., a distance therebetween, a size relationship therebetween, etc.). For instance, an inertial sensor 142 may be disposed on a vertebra that rotates in a first direction about a first axis. The computing device 102 may convert the measurements (e.g., rotation measurements) of the inertial sensors 142 into a respective rotation of the vertebra based on the physical relationship between the inertial sensor 142 and the vertebra. In an example, the physical relationship may be based on a configuration by which the inertial sensor 142 is mounted to the end of an elongated rod extending out of the vertebra.

In some implementations, the inertial sensors 142 may be connected to or coupled with the tracking markers 138. For instance, an inertial sensor 142 may be disposed within a tracking marker 138 (e.g., the tracking marker 138 includes an optical sphere that includes a hollow cavity, with the inertial sensor 142 disposed within the hollow cavity). The combination of the inertial sensors 142 and the tracking markers 138 may allow for a compact device to be disposed on or proximate to one or more anatomical elements to enable tracking any pose changes in the one or more anatomical elements during the course of a surgery or surgical procedure. In some other examples, the inertial sensors 142 may be electrically or physically coupled with the tracking markers 138, but spaced apart a distance from the tracking markers 138.

The database 130 may store information that correlates one coordinate system (e.g., one or more robotic coordinate systems) to another (e.g., a patient coordinate system, a navigation coordinate system, etc.). The database 130 may additionally or alternatively store, for example, one or more surgical plans (including, for example, pose information about a target and/or image information about a patient's anatomy at and/or proximate the surgical site, for use by the robot 114, the navigation system 118, and/or a user of the computing device 102 or of the system 100). In some cases, the database 130 may store one or more images in connection with a surgery to be completed by or with the assistance of one or more other components of the system 100. In some aspects, the database 130 may store any other information associated with the system 100, a surgical procedure, a patient's anatomy, etc.

The database 130 may be configured to provide any such information to the computing device 102 or to any other device of the system 100 or external to the system 100, for example, directly or indirectly (e.g., via the cloud network 134). In some implementations, the database 130 may be or may be associated with a hospital image storage system, such as a picture archiving and communication system (PACS), a health information system (HIS), and/or another system for collecting, storing, managing, and/or transmitting electronic medical records including image data.

In some aspects, the computing device 102 may communicate with a server(s) and/or a database (e.g., database 130) directly or indirectly over a communications network (e.g., the cloud network 134). The communications network may include any type of known communication medium or collection of communication media and may use any type of protocols to transport data between endpoints. The communications network may include wired communications technologies, wireless communications technologies, or any combination thereof.

Wired communications technologies may include, for example, Ethernet-based wired local area network (LAN) connections using physical transmission mediums (e.g., coaxial cable, copper cable/wire, fiber-optic cable, etc.). Wireless communications technologies may include, for example, cellular or cellular data connections and protocols (e.g., digital cellular, personal communications service (PCS), cellular digital packet data (CDPD), general packet radio service (GPRS), enhanced data rates for global system for mobile communications (GSM) evolution (EDGE), code division multiple access (CDMA), single-carrier radio transmission technology (1×RTT), evolution-data optimized (EVDO), high speed packet access (HSPA), universal mobile telecommunications service (UMTS), 3G, long term evolution (LTE), 4G, and/or 5G, etc.), Bluetooth®, Bluetooth® low energy, Wi-Fi, radio, satellite, infrared connections, and/or ZigBee® communication protocols.

The Internet is an example of the communications network that constitutes an Internet Protocol (IP) network consisting of multiple computers, computing networks, and other communication devices located in multiple locations, and components in the communications network (e.g., computers, computing networks, communication devices) may be connected through one or more telephone systems and other means. Other examples of the communications network may include, without limitation, a standard Plain Old Telephone System (POTS), an Integrated Services Digital Network (ISDN), the Public Switched Telephone Network (PSTN), a Local Area Network (LAN), a Wide Area Network (WAN), a wireless LAN (WLAN), a Session Initiation Protocol (SIP) network, a Voice over Internet Protocol (VoIP) network, a cellular network, and any other type of packet-switched or circuit-switched network known in the art. In some cases, the communications network 120 may include of any combination of networks or network types. In some aspects, the communications network may include any combination of communication mediums such as coaxial cable, copper cable/wire, fiber-optic cable, or antennas for communicating data (e.g., transmitting/receiving data).

The computing device 102 may be connected to the cloud network 134 via the communication interface 108, using a wired connection, a wireless connection, or both. In some implementations, the computing device 102 may communicate with the database 130 and/or an external device (e.g., a computing device) via the cloud network 134.

The system 100 or similar systems may be used, for example, to carry out one or more aspects of the method 400 described herein. The system 100 or similar systems may also be used for other purposes.

Figure 2A:
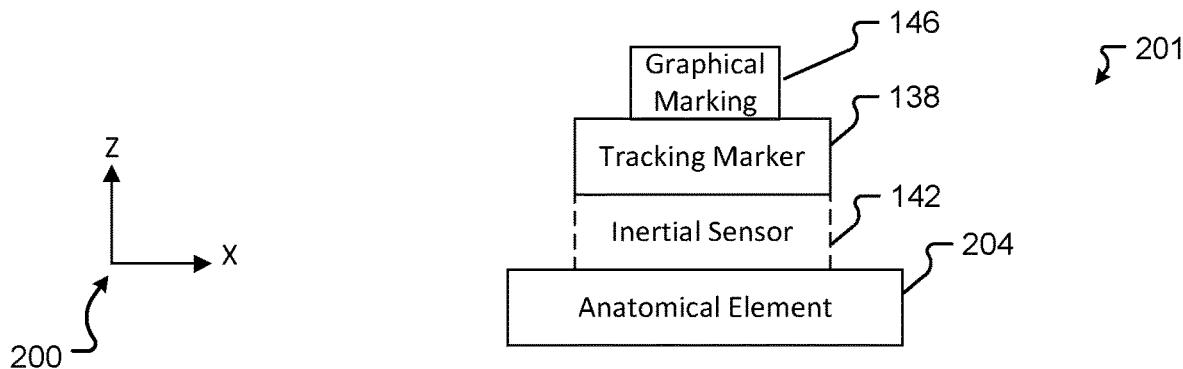
FIGS. 2A through 2C illustrate examples of tracking elements that support robot integrated segmental tracking in accordance with aspects of the present disclosure.
Figure 2B:
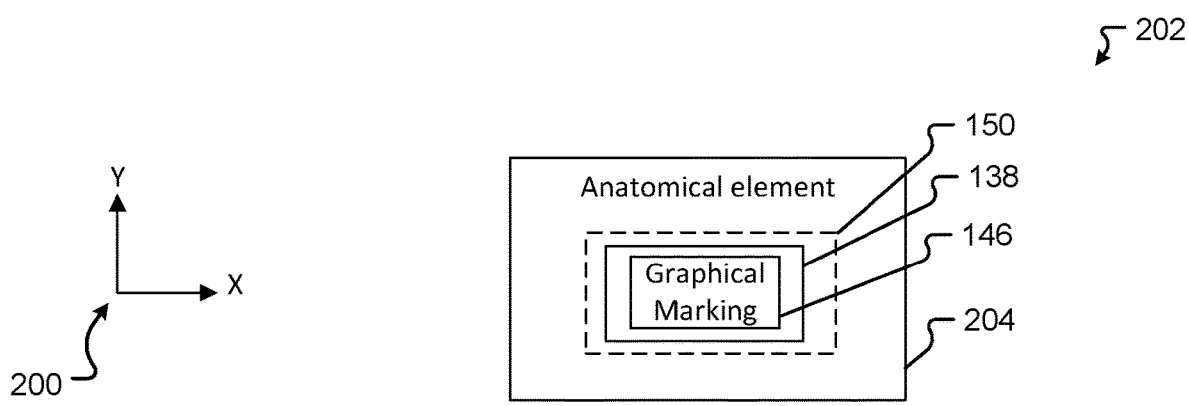
Figure 2C:
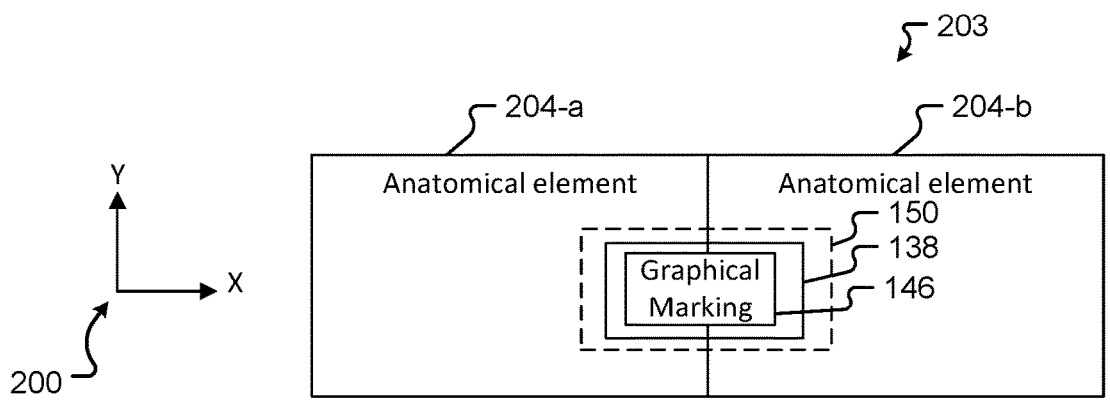

FIGS. 2A-2C illustrate example aspects of the system 100 in accordance with at least one implementation of the present disclosure. FIGS. 2A-2C illustrate examples 201 through 203 that support robot integrated segmental tracking in accordance with aspects of the present disclosure.

In the figures that follow, example features of the system 100 (e.g., tracking markers 138, inertial sensors 142, and graphical markings 146) are described in conjunction with a coordinate system 200. For example, in FIGS. 2A, 2B, and 2C that follow, example features and components (e.g., tracking markers 138, inertial sensors 142, and graphical markings 146) with respect to dimensions, positions, spacing, directionality, etc. of an object (e.g., anatomical element 204) are defined with respect to an X-axis, a Y-axis, and a Z-axis of the coordinate system 200.

As discussed herein, the system 100 may include one or more tracking markers 138 and one or more inertial sensors 142 that may be disposed a known physical distance from or in a known physical relationship with one or more anatomical elements 204. The anatomical elements 204 may be or may include organs, bones, portions thereof, or any portion of a human anatomy (e.g., a spinal column, a vertebra, etc.). The anatomical elements 204 may be portions of a patient upon which a surgery or surgical procedure is to be conducted (e.g., a vertebra upon which a vertebral fusion is to be performed, a vertebra to be drilled into to relieve pressure on a nerve). The quantity and type of the anatomical elements 204 may vary depending on, for example, the type of surgery or surgical procedure being performed. For instance, in some implementations the anatomical elements 204 include one or more vertebrae of the spine.

In some implementations, different spinal surgeries or surgical procedures may use or utilize any combination of the tracking markers 138, the inertial sensors 142, and/or the graphical markings 146. Aspects of the present disclosure support attaching and/or disposing any combination of the tracking markers 138, the inertial sensors 142, and/or the graphical markings 146 proximate different vertebrae. For example, a spinal fusion between the T6 and the T7 vertebrae may include placing and/or positioning a combination of tracking markers 138, inertial sensors 142, and/or graphical markings 146 on or proximate the T6 and T7 vertebrae, while a different spinal procedure on the T2 vertebra may include placing and/or positioning a combination of tracking markers 138, inertial sensors 142, and/or graphical markings 146 on the T1 and T3 vertebrae to track movement of the T2 vertebra during the surgical procedure.

FIG. 2A illustrates an example 201 that supports robot integrated segmental tracking in accordance with aspects of the present disclosure. In some implementations, a tracking marker 138 and an inertial sensor 142 may be integrated (e.g., paired) in a combined apparatus, and the tracking marker 138 and/or the inertial sensor 142 may be affixed or attached to an anatomical element 204. For example, the inertial sensor 142 may be disposed in the tracking marker 138, and the tracking marker 138 may be attached to one or more of the anatomical elements 204.

In some aspects, the tracking marker 138 may include a graphical marking 146 as described herein. The graphical marking 146 may be located on any surface (e.g., a top surface, a side surface, etc.) of the tracking marker 138. The tracking marker 138 may include any quantity of graphical markings 146. The tracking marker 138, the inertial sensor 142, and the graphical marking 146 may be any size (e.g., with respect to one another) and are not limited to the examples illustrated in FIG. 2A.

Additionally or alternatively, but not illustrated, an inertial sensor 142 may have a physical relationship with an anatomical element 204 and/or a tracking marker 138. Stated differently, the inertial sensor 142 may be indirectly attached to the anatomical element 204 and/or the tracking marker 138. For example, the inertial sensor 142 may be positioned a first distance from the anatomical element 204 and/or a second distance from a tracking marker 138 associated with (e.g., coupled to) the anatomical element 204. The values of the distances are in no way limited and may be, for example, 0.1 mm, 0.2 mm, 0.5 mm, 1 mm, 2 mm, 5 mm, 10 mm, 15 mm, 25 mm, 50 mm, 100 mm, 150 mm, 200 mm, 500 mm, etc.

FIG. 2B illustrates an example 202 that supports robot integrated segmental tracking in accordance with aspects of the present disclosure. The system 100 may compare real-time and previous locations of the anatomical element 204 based on a tracked area 150 (also referred to herein as a target area) of the anatomy. In some examples, the tracked area 150 may be indicated by the graphical marking 146, where the graphical marking 146 is detectable by the imaging device 112. In the example 202 of FIG. 2B, the graphical marking 150 is included the tracked area. For example, the tracked area 150 may be greater than or equal to the size (e.g., area, diameter, etc.) of the graphical marking 146 and/or the tracking marker 138.

In the example 202 of FIG. 2B, the graphical marking 146 is included the tracked area 150. For example, the tracked area 150 may be greater than or equal to the size (e.g., area, diameter, etc.) of the graphical marking 146 and/or the tracking marker 138. In some other aspects (not illustrated), the graphical marking 146 may be within a threshold distance (e.g., configured using the system 100) of the tracked area 150. For example, the graphical marking 146 may be offset (e.g., by a distance configured using the system 100) from the tracked area 150.

In some other examples, the tracked area 150 may be associated with the inertial sensor 142 (not illustrated in FIG. 2B) as detected by the system 100 (e.g., by the navigation system 118). In some examples, the system 100 may calculate positional information associated with the tracked area 150 based on movement information provided by the inertial sensor 142.

FIG. 2C illustrates an example 203 that supports robot integrated segmental tracking in accordance with aspects of the present disclosure.

In some implementations, the tracking marker 138, the inertial sensor 142 (not illustrated in FIG. 2C), and/or the graphical marking 146 may span or be connected across two or more anatomical elements 204 (e.g., anatomical element 204-a, anatomical element 204-b). The anatomical elements 204-a and 204-b, for example, may be or may include vertebrae. The inertial sensor 142 may be disposed (e.g., within the tracking marker 138, at a location spaced apart from the tracking marker 138, etc.) such that movement of the anatomical element 204-a and/or the anatomical element 204-b may be captured by the inertial sensor 142. In some aspects, the system 100 may compare real-time and previous locations of the anatomical element 204-a and the anatomical element 204-b based on the tracked area 150.

Additionally or alternatively, the tracking marker 138 may be positioned across (e.g., overlapping) the anatomical element 204-a and/or the anatomical element 206-b such that any movement of either the anatomical element 204-a or the anatomical element 204-b may result in the movement of the tracking marker 138. While FIG. 2C depicts two anatomical elements 204, it is to be understood that additional anatomical elements 204 may be tracked by or coupled together by additional inertial sensors 142 and/or the tracking markers 138.

In some aspects (later illustrated with reference to FIGS. 3A and 3B), the system 100 may support tracking multiple tracking markers 138 coupled to the anatomy (e.g., multiple tracking markers 138 attached to different respective anatomical elements 204).

Figure 3A:
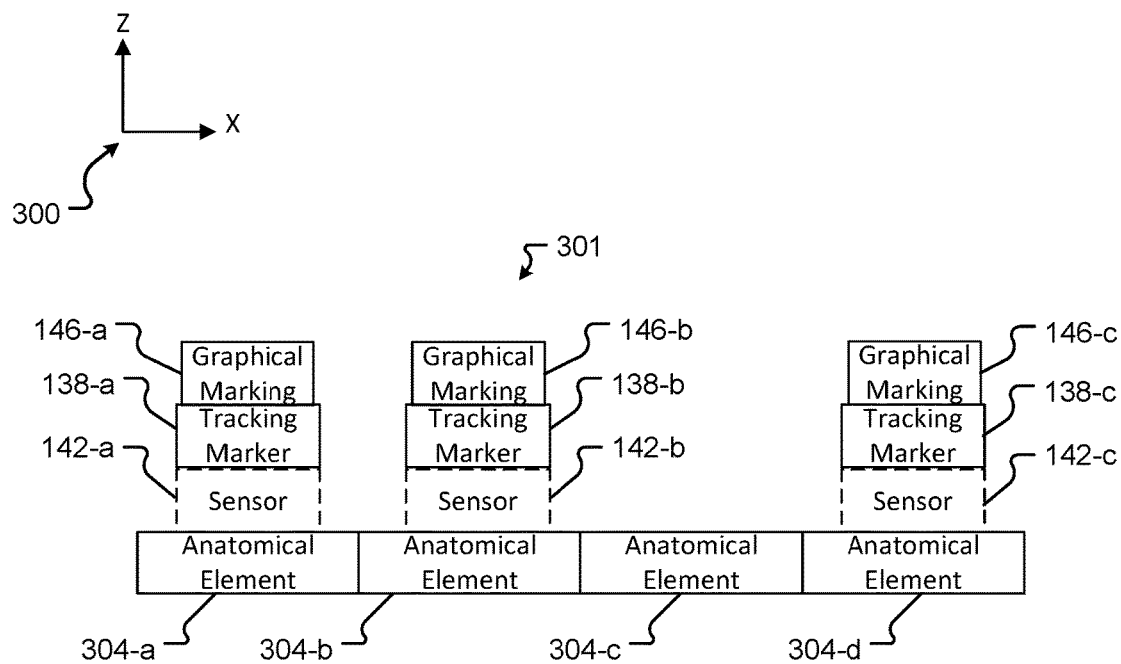
FIGS. 3A and 3B illustrate examples of tracking elements positioned at an anatomical element in accordance with aspects of the present disclosure.
Figure 3B:
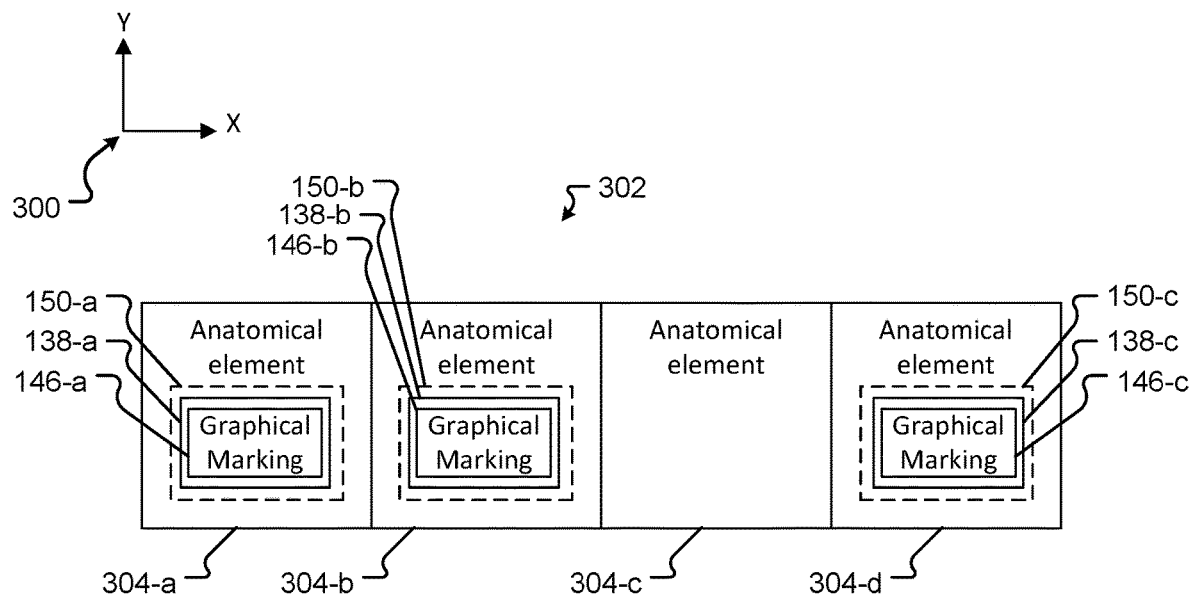

FIGS. 3A and 3B illustrate example aspects of the system 100 in accordance with aspects of the present disclosure. FIGS. 3A and 3B illustrate examples 301 through 302 that support robot integrated segmental tracking in accordance with aspects of the present disclosure.

In the figures that follow, example features of the system 100 (e.g., tracking markers 138, inertial sensors 142, and graphical markings 146) are described in conjunction with a coordinate system 300, which may be the same as the coordinate system 300 described with reference to FIGS. 2A through 2C. For example, in FIGS. 3A and 3B that follow, example features and components (e.g., tracking markers 138, inertial sensors 142, and graphical markings 146) with respect to dimensions, positions, spacing, directionality, etc. of an object (e.g., anatomical element 204) are defined with respect to an X-axis, a Y-axis, and a Z-axis of the coordinate system 300.

Referring to FIGS. 3A and 3B, the system 100 may support tracking multiple tracking markers 138 (e.g., tracking marker 138-a, tracking marker 138-b) coupled to the anatomy. For example, among anatomical element 304-a through anatomical element 304-d, the tracking marker 138-a and the tracking marker 138-b may be respectively attached to anatomical element 304-a and anatomical element 304-d. Anatomical element 304-a through anatomical element 304-d may be examples of an anatomical element 204 described herein.

While FIGS. 3A and 3B depict two tracking markers 138 (e.g., tracking marker 138-a, tracking marker 138-b), two graphical markings 146 (e.g., graphical marking 146-a, graphical marking 146-b), and four anatomical elements 304 (e.g., anatomical element 304-a through anatomical element 304-d), it is to be understood that any combination of tracking markers 138 (and associated inertial sensors 142), graphical markings 146, and anatomical elements 304 may be present.

Referring to FIGS. 3A and 3B, the imaging device 112 (or multiple imaging devices 112) of the system 100 may capture image data of the anatomical elements 304, graphical markings 146, and/or the tracking markers 138. The imaging device 112 may provide the image data to one or more components of the system 100 (e.g., the navigation system 118). Additionally, or alternatively, the system 100 (e.g., navigation system 118) may capture movement information associated with the inertial sensors 142. The navigation system 118 may generate signals associated with controlling the operation or movement of a surgical tool based on the image data and/or movement information.

In some implementations, during the course of a surgery or surgical procedure, one or more of the anatomical elements 304 (e.g., any of anatomical element 304-a through anatomical element 304-d) may move. For instance, an anatomical element 304 (e.g., anatomical element 304-a) may experience a movement relative to another anatomical element 304 (e.g., anatomical element 304-b). The movement 316 may be caused by, for example, forces and/or vibrations caused by the operation of a surgical tool; forces generated by movement of another anatomical element; movement of a surgical bed upon which the patient is resting or the movement of any other surgical component; combinations thereof; and/or the like.

The movement of the anatomical element 304-b may be captured by the imaging device 112 and the navigation system 118 (e.g., based on image data and/or movement information as described herein). In an example, the system 100 may determine the movement of the tracking marker 138-b and/or the inertial sensor 142-b relative to, for example, the tracking marker 138-a, the inertial sensor 142-a, and/or the anatomical element 304-a. The movement of the anatomical element 304-b may be a translational movement (e.g., movement of the anatomical element 304-b relative to the anatomical element 304-a in a first direction along a first axis), rotational movement (e.g., rotation of the anatomical element 304-b relative to the anatomical element 304-a about a first internal axis, rotation of the anatomical element 304-b relative to the anatomical element 304-a about a first axis of the anatomical element 304-a), combinations thereof, and/or the like. The captured movement may be used by the navigation system 118 (or other component of the system 100 such as the computing device 102) to determine a new pose of the anatomical element 304-b and adjust the surgery or surgical procedure accordingly.

As an example, the anatomical elements 304-a through 304-d may be or may include vertebrae, with a spinal surgery or surgical procedure being performed thereon. During the course of a spinal fusion, for example, the navigation system 118 may navigate or otherwise operate a surgical tool (e.g., a drill) held by the robotic arm 116. As the surgical tool drills into the anatomical element 304-a, the anatomical element 304-b may experience movement relative to the anatomical element 304-a (e.g., the torque generated by the surgical tool may generate a force resulting in movement of the anatomical element 304-b). The movement of the anatomical element 304-b may, in some surgeries, negatively impact the surgery or surgical procedure (e.g., result in a loss of alignment between anatomical element 304-a and anatomical element 304-b).

In an example, the system 100 may determine movement of the anatomical element 304-b based on image data provided by the imaging device 112 (e.g., captured images/image data depicting movement of the tracking marker 138-b), and/or by movement information (e.g., measurements) associated with the movement of the inertial sensor 142-b.

In some implementations, using the image data and/or movement information the navigation system 118 (using, for example, image processing 120 and/or segmentation 122) may determine a translational movement of the anatomical element 304-b relative to the anatomical element 304-a. Similarly, the navigation system 118 may, using one or more transformations 124, may process measurements or readings generated by the inertial sensor 142-b and determine a rotational movement of the anatomical element 304-b relative to the anatomical element 304-a. Using the determined rotational movement of the anatomical element 304-b, the navigation system 118 may be able to further update the registration of the anatomical element 304-b to the surgical tool and/or adjust the surgical plan based on the movement of the anatomical element 304-b.

Aspects described herein, though described with reference to anatomical element 304-a and anatomical element 304-b, may similarly be applied to any combination of anatomical elements 304 (e.g., anatomical element 304-a and anatomical element 304-c, anatomical element 304-b through anatomical element 304-d, etc.).

As described herein (e.g., reference to FIGS. 1 through 3), aspects of the present disclosure support utilizing the imaging device 112 in association with capturing images (image data) for periodically assessing whether any shifts have occurred. In an example, the system 100 may support assessing for shifts between a coordinate system associated with the system 100 (or the robot 114) and a coordinate system associated with registered anatomical elements (e.g., anatomical elements 204, anatomical elements 304). In another example, the system 100 may support assessing for shifts between a registered position and/or orientation of an anatomical element and a real-time position and/or orientation of the anatomical element.

The system 100 may alert an operator of the system of any detected shifts. In some aspects, the system 100 may provide notifications (e.g., via user interface 110) to the operator for maneuvering a robotic arm(s) 116 in association with a surgical operation.

Using the imaging device 112, the system 100 may compare real-time locations and previous locations of anatomical elements (e.g., organs, etc.) of a patient. In an example, the system 110 may compare the real-time and previous locations of the anatomical elements using captured 3D images, for example, by scanning an entire 3D image(s) of the anatomy of the patient (e.g., in open surgery). For example, during open surgery, a relatively clear (e.g., unobstructed) line of sight to the anatomy and anatomy connectors is available, and the system 100 may track both the anatomy and the anatomy connectors using the imaging device 112.

Additionally, or alternatively, the system 100 may compare real-time and previous locations of the anatomical elements using 3D tracking information obtained from tracking devices (e.g., tracking markers 138, inertial sensors 142, etc.) coupled to the anatomy (e.g., in minimally MIS, open surgery, etc.). For example, aspects of the present disclosure support tracking multiple tracking markers 138 coupled to the anatomy (e.g., multiple tracking markers 138 attached to different respective anatomical elements). In some aspects, the tracking devices may be rigidly connected to the anatomy.

Accordingly, for example, aspects of the present disclosure may support multiple layers of sensing (e.g., using captured 3D images, tracking markers 138, inertial sensors 142, graphical markings 146, etc.). Using the multiple layers of sensing, the system 100 may alert a user (e.g., an operator, a patient, etc.) of any shift (e.g., between different coordinate systems, between a registered anatomy location and an actual anatomy location). For example, the system 100 may alert the user of any shift between registered locations of an anatomical element(s) (e.g., vertebra, vertebrae, etc.) and real-time locations of corresponding tracking markers 138.

Using the multiple layers of sensing, the system 100 may compensate for such shifts. For example, the system 100 may maneuver a robotic arm 116 and/or a surgical tool so as to compensate for a deviation value associated with any such shifts.

Figure 4:
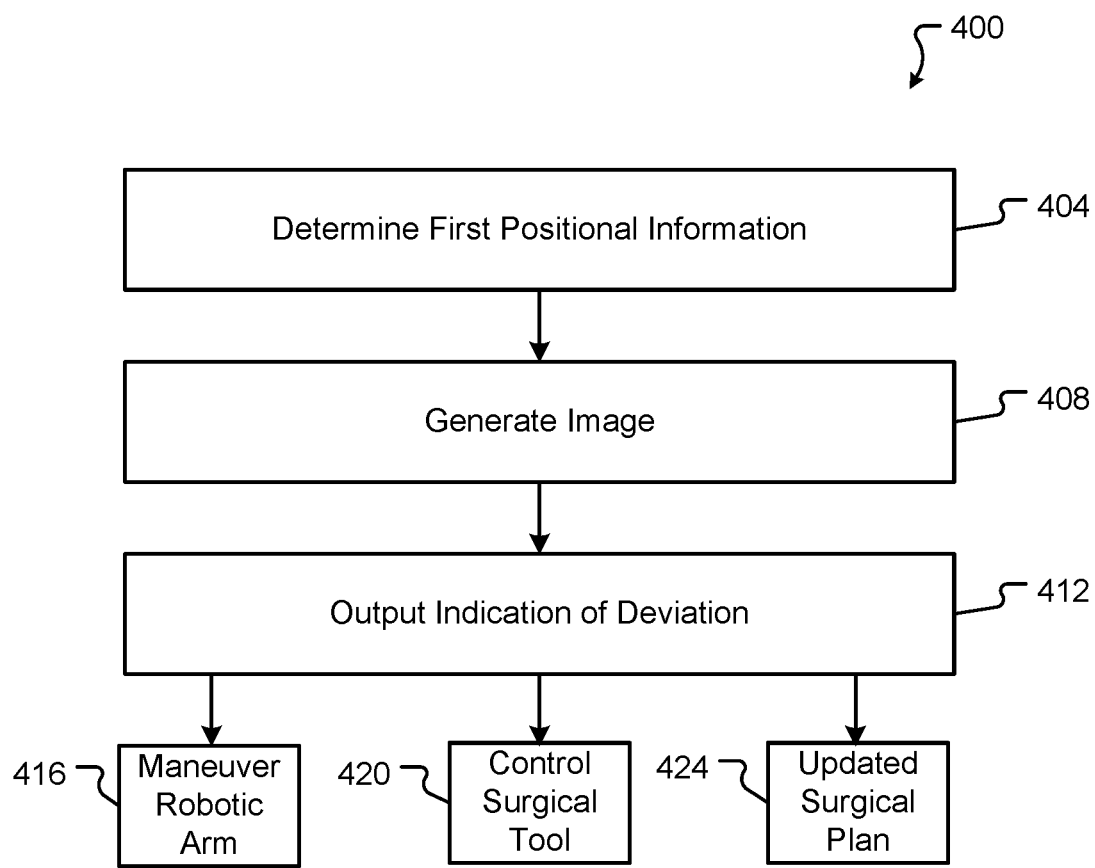
FIG. 4 illustrates an example of a process flow that supports robot integrated segmental tracking in accordance with aspects of the present disclosure.

FIG. 4 illustrates an example of a process flow 400 that supports robot integrated segmental tracking in accordance with aspects of the present disclosure. In some examples, process flow 400 may implement aspects of system 100 described with reference to FIGS. 1 through 3. Further, process flow 400 may be implemented by a computing device 102, an imaging device 112, a robot 114, and/or a navigation system 118 (and components thereof) as described with reference to FIGS. 1 through 3.

In the following description of the process flow 400, the operations may be performed in a different order than the order shown, or the operations may be performed in different orders or at different times. Certain operations may also be left out of the process flow 400, or other operations may be added to the process flow 400. It is to be understood that any device (e.g., any device associated with the system 100) may perform the operations of the process flow 400.

At 404, the process flow 400 includes determining first positional information of one or more objects based on three-dimensional first image data captured by an imaging device (e.g., imaging device 112), tracking information associated with the one or more objects, or both. In some aspects, the first positional information may include a real-time location of the one or more objects. In some aspects, the one or more objects may include at least one anatomical element (e.g., an anatomical element 204, an anatomical element 304).

In some aspects, the tracking information is associated with a tracking device (e.g., tracking marker 138, inertial sensor 142) coupled to the one or more objects; and the tracking information may include at least one of movement information, positional information, and orientation information associated with the tracking device. In some aspects, the tracking device may include at least one of a spherical shaped element, a polygonal shaped element, a squircular shaped element, and a graphical marking (e.g., graphical marking 146). In some aspects, the tracking device may include at least one substantially non-reflective surface.

In some aspects, the tracking information corresponds to a tracked area (e.g., tracked area 150) associated with the one or more objects; and the tracking information may include at least one of movement information, positional information, and orientation information associated with the tracked area.

In some aspects, (not illustrated), the process flow 400 includes tracking at least one of the movement information, the positional information, and the orientation information associated with the tracked area based on at least one of: a tracking device (e.g., tracking marker 138) coupled to the one or more objects; and a graphical marking (e.g., graphical marking 146) associated with the tracking device, the tracked area, or both. In some aspects, the graphical marking is included in the tracking device, included the tracked area, within a threshold distance of the tracked area, or any combination thereof.

At 408, the process flow 400 includes generating an image including a graphical representation of the one or more objects. In some aspects, generating the image may include positioning the graphical representation of the one or more objects based on a comparison result indicative of a deviation between the first positional information and reference positional information of the one or more objects. In some aspects, the reference positional information may include a registered location of the one or more objects.

In some aspects, the deviation between the first positional information and the reference positional information may include at least one of: a distance value; an orientation value; and a movement value.

In some aspects, the first positional information and the reference positional information are associated with at least one of: a first coordinate system associated with a robot device (e.g., robot 114) included in the system; and a second coordinate system associated with the one or more objects.

At 412, the process flow 400 includes outputting an indication (e.g., via a user interface 110) of the deviation between the first positional information and the reference positional information.

In some aspects, the one or more objects may include a first object (e.g., anatomical element 204-*a*, anatomical element 304-*a*. etc.) and a second object (e.g., anatomical element 204-*b*, anatomical element 304-*b*, etc.); and the tracking information is associated with at least one of: first tracking device coupled to the first object; a second tracking device coupled to the second object; a first tracked area associated with the first object; and a second tracked area associated with the second object.

In some aspects, at 416, the process flow 400 includes maneuvering a robotic arm of the system based on at least one of: a first value associated with the deviation; and a second value associated with compensating for the deviation.

In some aspects, at 420, the process flow 400 includes controlling at least one surgical tool based on at least one of: a first value associated with the deviation; and a second value associated with compensating for the deviation.

In some aspects, at 424, the process flow 400 includes updating a surgical plan based on at least one of: a first value associated with the deviation; and a second value associated with compensating for the deviation.

Any of the steps, functions, and operations discussed herein can be performed continuously and automatically.

The exemplary systems and methods of this disclosure have been described in relation to examples of a system 100 (e.g., a computing device 102, an imaging device 112, a robot 114, a navigation system 118, a tracking marker 138, an inertial sensor 142, a graphical marking 146, etc.). However, to avoid unnecessarily obscuring the present disclosure, the preceding description omits a number of known structures and devices. This omission is not to be construed as a limitation of the scope of the claimed disclosure. Specific details are set forth to provide an understanding of the present disclosure. It should, however, be appreciated that the present disclosure may be practiced in a variety of ways beyond the specific detail set forth herein.

Furthermore, while the exemplary implementations illustrated herein show the various components of the system collocated, certain components of the system can be located remotely, at distant portions of a distributed network, such as a LAN and/or the Internet, or within a dedicated system. Thus, it should be appreciated, that the components of the system can be combined into one or more devices, such as a server, communication device, or collocated on a particular node of a distributed network, such as an analog and/or digital telecommunications network, a packet-switched network, or a circuit-switched network. It will be appreciated from the preceding description, and for reasons of computational efficiency, that the components of the system can be arranged at any location within a distributed network of components without affecting the operation of the system.

Furthermore, it should be appreciated that the various links connecting the elements can be wired or wireless links, or any combination thereof, or any other known or later developed element(s) that is capable of supplying and/or communicating data to and from the connected elements. These wired or wireless links can also be secure links and may be capable of communicating encrypted information. Transmission media used as links, for example, can be any suitable carrier for electrical signals, including coaxial cables, copper wire, and fiber optics, and may take the form of acoustic or light waves, such as those generated during radio-wave and infra-red data communications.

While the flowcharts have been discussed and illustrated in relation to a particular sequence of events, it should be appreciated that changes, additions, and omissions to this sequence can occur without materially affecting the operation of the disclosed implementations, configuration, and aspects.

A number of variations and modifications of the disclosure can be used. It would be possible to provide for some features of the disclosure without providing others.

In yet another implementation, the systems and methods of this disclosure can be implemented in conjunction with a special purpose computer, a programmed microprocessor or microcontroller and peripheral integrated circuit element(s), an ASIC or other integrated circuit, a digital signal processor, a hard-wired electronic or logic circuit such as discrete element circuit, a programmable logic device or gate array such as PLD, PLA, FPGA, PAL, special purpose computer, any comparable means, or the like. In general, any device(s) or means capable of implementing the methodology illustrated herein can be used to implement the various aspects of this disclosure. Exemplary hardware that can be used for the present disclosure includes computers, handheld devices, telephones (e.g., cellular, Internet enabled, digital, analog, hybrids, and others), and other hardware known in the art. Some of these devices include processors (e.g., a single or multiple microprocessors), memory, nonvolatile storage, input devices, and output devices. Furthermore, alternative software implementations including, but not limited to, distributed processing or component/object distributed processing, parallel processing, or virtual machine processing can also be constructed to implement the methods described herein.

In yet another implementation, the disclosed methods may be readily implemented in conjunction with software using object or object-oriented software development environments that provide portable source code that can be used on a variety of computer or workstation platforms. Alternatively, the disclosed system may be implemented partially or fully in hardware using standard logic circuits or VLSI design. Whether software or hardware is used to implement the systems in accordance with this disclosure is dependent on the speed and/or efficiency requirements of the system, the particular function, and the particular software or hardware systems or microprocessor or microcomputer systems being utilized.

In yet another implementation, the disclosed methods may be partially implemented in software that can be stored on a storage medium, executed on programmed general-purpose computer with the cooperation of a controller and memory, a special purpose computer, a microprocessor, or the like. In these instances, the systems and methods of this disclosure can be implemented as a program embedded on a personal computer such as an applet, JAVA® or CGI script, as a resource residing on a server or computer workstation, as a routine embedded in a dedicated measurement system, system component, or the like. The system can also be implemented by physically incorporating the system and/or method into a software and/or hardware system.

Although the present disclosure describes components and functions implemented in the implementations with reference to particular standards and protocols, the disclosure is not limited to such standards and protocols. Other similar standards and protocols not mentioned herein are in existence and are considered to be included in the present disclosure. Moreover, the standards and protocols mentioned herein and other similar standards and protocols not mentioned herein are periodically superseded by faster or more effective equivalents having essentially the same functions. Such replacement standards and protocols having the same functions are considered equivalents included in the present disclosure.

The present disclosure, in various implementations, configurations, and aspects, includes components, methods, processes, systems and/or apparatus substantially as depicted and described herein, including various implementations, subcombinations, and subsets thereof. Those of skill in the art will understand how to make and use the systems and methods disclosed herein after understanding the present disclosure. The present disclosure, in various implementations, configurations, and aspects, includes providing devices and processes in the absence of items not depicted and/or described herein or in various implementations, configurations, or aspects hereof, including in the absence of such items as may have been used in previous devices or processes, e.g., for improving performance, achieving ease, and/or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more implementations, configurations, or aspects for the purpose of streamlining the disclosure. The features of the implementations, configurations, or aspects of the disclosure may be combined in alternate implementations, configurations, or aspects other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed implementation, configuration, or aspect. Thus, the following claims are hereby incorporated into this Detailed Description, with each claim standing on its own as a separate preferred implementation of the disclosure.

Moreover, though the description of the disclosure has included description of one or more implementations, configurations, or aspects and certain variations and modifications, other variations, combinations, and modifications are within the scope of the disclosure, e.g., as may be within the skill and knowledge of those in the art, after understanding the present disclosure. It is intended to obtain rights, which include alternative implementations, configurations, or aspects to the extent permitted, including alternate, interchangeable and/or equivalent structures, functions, ranges, or steps to those claimed, whether or not such alternate, interchangeable and/or equivalent structures, functions, ranges, or steps are disclosed herein, and without intending to publicly dedicate any patentable subject matter.

Example aspects of the present disclosure include:

A system including: a processor; and a memory storing instructions thereon that, when executed by the processor, cause the processor to: determine first positional information of one or more objects based on three-dimensional first image data captured by an imaging device, tracking information associated with the one or more objects, or both, where the first positional information includes a real-time location of the one or more objects; generate an image including a graphical representation of the one or more objects, where generating the image includes positioning the graphical representation of the one or more objects based on a comparison result indicative of a deviation between the first positional information and reference positional information of the one or more objects, where the reference positional information includes a registered location of the one or more objects; and output an indication of the deviation between the first positional information and the reference positional information.

In some aspects, the tracking information is associated with a tracking device coupled to the one or more objects; and the tracking information includes at least one of movement information, positional information, and orientation information associated with the tracking device.

In some aspects, the tracking device includes at least one of a spherical shaped element, a polygonal shaped element, a squircular shaped element, and a graphical marking.

In some aspects, the tracking device includes at least one substantially non-reflective surface.

In some aspects, the tracking information corresponds to a tracked area associated with the one or more objects; and the tracking information includes at least one of movement information, positional information, and orientation information associated with the tracked area.

In some aspects, the instructions are further executable by the processor to: track at least one of the movement information, the positional information, and the orientation information associated with the tracked area based on at least one of: a tracking device coupled to the one or more objects; and a graphical marking associated with the tracking device, the tracked area, or both. In some aspects, the graphical marking is included in the tracking device, included the tracked area, within a threshold distance of the tracked area, or any combination thereof.

In some aspects, the one or more objects includes a first object and a second object; and the tracking information is associated with at least one of: first tracking device coupled to the first object; a second tracking device coupled to the second object; a first tracked area associated with the first object; and a second tracked area associated with the second object.

In some aspects, the one or more objects include at least one anatomical element.

In some aspects, the deviation between the first positional information and the reference positional information includes at least one of: a distance value; an orientation value; and a movement value.

In some aspects, the first positional information and the reference positional information are associated with at least one of: a first coordinate system associated with a robot device included in the system; and a second coordinate system associated with the one or more objects.

In some aspects, the instructions are further executable by the processor to: maneuver a robotic arm of the system based on at least one of: a first value associated with the deviation; and a second value associated with compensating for the deviation.

In some aspects, the instructions are further executable by the processor to: control at least one surgical tool based on at least one of: a first value associated with the deviation; and a second value associated with compensating for the deviation.

In some aspects, the instructions are further executable by the processor to: update a surgical plan based on at least one of: a first value associated with the deviation; and a second value associated with compensating for the deviation.

A method including: determining first positional information of one or more objects based on three-dimensional first image data captured by an imaging device, tracking information associated with the one or more objects, or both, where the first positional information includes a real-time location of the one or more objects; generating an image including a graphical representation of the one or more objects, where generating the image includes positioning the graphical representation of the one or more objects based on a comparison result indicative of a deviation between the first positional information and reference positional information of the one or more objects, where the reference positional information includes a registered location of the one or more objects; and outputting an indication of the deviation between the first positional information and the reference positional information.

In some aspects, the tracking information is associated with a tracking device coupled to the one or more objects; and the tracking information includes at least one of movement information, positional information, and orientation information associated with the tracking device.

In some aspects, the tracking device includes at least one of a spherical shaped element, a polygonal shaped element, an equicrural shaped element, and a graphical marking.

In some aspects, the tracking device includes at least one substantially non-reflective surface.

A system including: an imaging device; a tracking device coupled to one or more objects; a processor; and a memory storing data thereon that, when processed by the processor, cause the processor to: determine first positional information of the one or more objects based on three-dimensional first image data captured by the imaging device, tracking information associated with the one or more objects, or both, where the first positional information includes a real-time location of the one or more objects; generate an image including a graphical representation of the one or more objects, where generating the image includes positioning the graphical representation of the one or more objects based on a comparison result indicative of a deviation between the first positional information and reference positional information of the one or more objects, where the reference positional information includes a registered location of the one or more objects; and output an indication of the deviation between the first positional information and the reference positional information.

In some aspects, the tracking information is associated with the tracking device coupled to the one or more objects; and the tracking information includes at least one of movement information, positional information, and orientation information associated with the tracking device.

In some aspects, the tracking device includes at least one of a spherical shaped element, a polygonal shaped element, a squircular shaped element, and a graphical marking.

In some aspects, the tracking device includes at least one substantially non-reflective surface.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/implementations in combination with any one or more other aspects/features/implementations.

Use of any one or more of the aspects or features as disclosed herein.

It is to be appreciated that any feature described herein can be claimed in combination with any other feature(s) as described herein, regardless of whether the features come from the same described implementation.

The phrases "at least one," "one or more," "or," and "and/or" are open-ended expressions that are both conjunctive and disjunctive in operation. For example, each of the expressions "at least one of A, B and C," "at least one of A, B, or C," "one or more of A, B, and C," "one or more of A, B, or C," "A, B, and/or C," and "A, B, or C" means A alone, B alone, C alone, A and B together, A and C together, B and C together, or A, B and C together.

The term "a" or "an" entity refers to one or more of that entity. As such, the terms "a" (or "an"), "one or more," and "at least one" can be used interchangeably herein. It is also to be noted that the terms "comprising," "including," and "having" can be used interchangeably.

The term "automatic" and variations thereof, as used herein, refers to any process or operation, which is typically continuous or semi-continuous, done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material."

Aspects of the present disclosure may take the form of an implementation that is entirely hardware, an implementation that is entirely software (including firmware, resident software, micro-code, etc.) or an implementation combining software and hardware aspects that may all generally be referred to herein as a "circuit," "module," or "system." Any combination of one or more computer-readable medium(s) may be utilized. The computer-readable medium may be a computer-readable signal medium or a computer-readable storage medium.

A computer-readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer-readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer-readable storage medium may be any tangible medium that can contain or store a program for use by or in connection with an instruction execution system, apparatus, or device.

A computer-readable signal medium may include a propagated data signal with computer-readable program code embodied therein, for example, in baseband or as part of a carrier wave. Such a propagated signal may take any of a variety of forms, including, but not limited to, electro-magnetic, optical, or any suitable combination thereof. A computer-readable signal medium may be any computer-readable medium that is not a computer-readable storage medium and that can communicate, propagate, or transport a program for use by or in connection with an instruction execution system, apparatus, or device. Program code embodied on a computer-readable medium may be transmitted using any appropriate medium, including, but not limited to, wireless, wireline, optical fiber cable, RF, etc., or any suitable combination of the foregoing.

The terms "determine," "calculate," "compute," and variations thereof, as used herein, are used interchangeably and include any type of methodology, process, mathematical operation or technique.

What is claimed is:

1. A system comprising:
a processor; and
a memory storing instructions thereon that, when executed by the processor, cause the processor to:
determine first positional information of one or more objects based at least in part on three-dimensional first image data captured by an imaging device, tracking information associated with the one or more objects, or both, wherein the first positional information comprises a real-time location of the one or more objects;
generate an image comprising a graphical representation of the one or more objects, wherein generating the image comprises positioning the graphical representation of the one or more objects based at least in part on a comparison result indicative of a deviation between the first positional information and reference positional information of the one or more objects, wherein the reference positional information comprises a registered location of the one or more objects; and
output an indication of the deviation between the first positional information and the reference positional information.

2. The system of claim 1, wherein:
the tracking information is associated with a tracking device coupled to the one or more objects; and
the tracking information comprises at least one of movement information, positional information, and orientation information associated with the tracking device.

3. The system of claim 2, wherein the tracking device comprises at least one of a spherical shaped element, a polygonal shaped element, a squircular shaped element, and a graphical marking.

4. The system of claim 2, wherein the tracking device comprises at least one substantially non-reflective surface.

5. The system of claim 1, wherein:
the tracking information corresponds to a tracked area associated with the one or more objects; and
the tracking information comprises at least one of movement information, positional information, and orientation information associated with the tracked area.

6. The system of claim 5, wherein the instructions are further executable by the processor to:
track at least one of the movement information, the positional information, and the orientation information associated with the tracked area based at least in part on at least one of:
a tracking device coupled to the one or more objects; and
a graphical marking associated with the tracking device, the tracked area, or both,
wherein the graphical marking is included in the tracking device, included in the tracked area, within a threshold distance of the tracked area, or any combination thereof.

7. The system of claim 1, wherein:
the one or more objects comprises a first object and a second object; and
the tracking information is associated with at least one of:
a first tracking device coupled to the first object;
a second tracking device coupled to the second object;
a first tracked area associated with the first object; and
a second tracked area associated with the second object.

8. The system of claim 1, wherein the one or more objects comprise at least one anatomical element.

9. The system of claim 1, wherein the deviation between the first positional information and the reference positional information comprises at least one of:
a distance value;
an orientation value; and
a movement value.

10. The system of claim 1, wherein the first positional information and the reference positional information are associated with at least one of:
a first coordinate system associated with a robot device included in the system; and
a second coordinate system associated with the one or more objects.

11. The system of claim 1, wherein the instructions are further executable by the processor to:
maneuver a robotic arm of the system based at least in part on at least one of:
a first value associated with the deviation; and
a second value associated with compensating for the deviation.

12. The system of claim 1, wherein the instructions are further executable by the processor to:
control at least one surgical tool based at least in part on at least one of:
a first value associated with the deviation; and
a second value associated with compensating for the deviation.

13. The system of claim 1, wherein the instructions are further executable by the processor to:
update a surgical plan based at least in part on at least one of:
a first value associated with the deviation; and
a second value associated with compensating for the deviation.

14. A method comprising:
determining first positional information of one or more objects based at least in part on three-dimensional first image data captured by an imaging device, tracking information associated with the one or more objects, or both, wherein the first positional information comprises a real-time location of the one or more objects;
generating an image comprising a graphical representation of the one or more objects, wherein generating the image comprises positioning the graphical representation of the one or more objects based at least in part on a comparison result indicative of a deviation between the first positional information and reference positional information of the one or more objects, wherein the reference positional information comprises a registered location of the one or more objects; and
outputting an indication of the deviation between the first positional information and the reference positional information.

15. The method of claim 14, wherein:
the tracking information is associated with a tracking device coupled to the one or more objects; and
the tracking information comprises at least one of movement information, positional information, and orientation information associated with the tracking device.

16. The method of claim 15, wherein the tracking device comprises at least one of a spherical shaped element, a polygonal shaped element, a squircular shaped element, and a graphical marking.

17. The method of claim 15, wherein the tracking device comprises at least one substantially non-reflective surface.

18. A system comprising:
an imaging device;
a tracking device coupled to one or more objects;
a processor; and
a memory storing data thereon that, when processed by the processor, cause the processor to:
determine first positional information of the one or more objects based at least in part on three-dimensional first image data captured by the imaging device, tracking information associated with the one or more objects, or both, wherein the first positional information comprises a real-time location of the one or more objects;
generate an image comprising a graphical representation of the one or more objects, wherein generating the image comprises positioning the graphical representation of the one or more objects based at least in part on a comparison result indicative of a deviation between the first positional information and reference positional information of the one or more objects, wherein the reference positional information comprises a registered location of the one or more objects; and output an indication of the deviation between the first positional information and the reference positional information.

19. The system of claim 18, wherein:

the tracking information is associated with the tracking device coupled to the one or more objects; and the tracking information comprises at least one of movement information, positional information, and orientation information associated with the tracking device.

20. The system of claim 19, wherein the tracking device comprises at least one of a spherical shaped element, a polygonal shaped element, a squircular shaped element, and a graphical marking.

21. The system of claim 19, wherein the tracking device comprises at least one substantially non-reflective surface.

* * * * *